United States Patent
Northcott et al.

(10) Patent No.: US 8,092,021 B1
(45) Date of Patent: *Jan. 10, 2012

(54) ON-AXIS ILLUMINATION FOR IRIS IMAGING

(75) Inventors: Malcolm J. Northcott, Felton, CA (US); J. Elon Graves, Los Gatos, CA (US)

(73) Assignee: AOptix Technologies, Inc., Campbell, CA (US)

( * ) Notice: Subject to any disclaimer, the term of this patent is extended or adjusted under 35 U.S.C. 154(b) by 469 days.

This patent is subject to a terminal disclaimer.

(21) Appl. No.: 12/021,189

(22) Filed: Jan. 28, 2008

Related U.S. Application Data (60) Provisional application No. 60/886,888, filed on Jan. 26, 2007.

(51) Int. Cl.
*A61B 3/14* (2006.01)
*A61B 3/10* (2006.01)

(52) U.S. Cl. ........................ 351/206; 351/221

(58) Field of Classification Search .................. 351/206, 351/210, 213, 221
See application file for complete search history.

(56) References Cited

U.S. PATENT DOCUMENTS

| | | | |
|---|---|---|---|
| 4,106,856 A * | 8/1978 | Babish | 359/602 |
| 5,098,426 A | 3/1992 | Sklar et al. | |
| 5,214,455 A | 5/1993 | Penney et al. | |
| 5,262,871 A | 11/1993 | Wilder et al. | |
| D389,723 S | 1/1998 | Godard et al. | |
| 5,956,122 A | 9/1999 | Doster | |
| 6,055,322 A | 4/2000 | Salganicoff et al. | |
| 6,059,773 A | 5/2000 | Maloney et al. | |
| 6,139,145 A | 10/2000 | Israel | |
| 6,333,988 B1 | 12/2001 | Seal et al. | |
| 6,447,119 B1 | 9/2002 | Stewart et al. | |
| 6,452,145 B1 | 9/2002 | Graves et al. | |
| 6,464,364 B2 | 10/2002 | Graves et al. | |
| 6,547,395 B1 | 4/2003 | Neal et al. | |
| 6,568,647 B2 | 5/2003 | Graves et al. | |
| 6,609,794 B2 | 8/2003 | Levine | |
| 6,714,665 B1 | 3/2004 | Hanna et al. | |
| 6,721,510 B2 | 4/2004 | Graves et al. | |
| 6,785,406 B1 | 8/2004 | Kamada | |
| 7,075,553 B2 | 7/2006 | Miller et al. | |
| 7,111,938 B2 | 9/2006 | Andino et al. | |
| 7,146,983 B1 | 12/2006 | Hohla et al. | |
| 7,237,898 B1 | 7/2007 | Hohla et al. | |
| 7,248,720 B2 | 7/2007 | Muller et al. | |
| 7,268,937 B1 | 9/2007 | Andersen et al. | |

(Continued)

OTHER PUBLICATIONS

*HBOX™ Specifications*, [online], 2007, 1 page, retrieved from the URL:<www.hoyosgroup.com>.

(Continued)

*Primary Examiner* — Ricky Mack
*Assistant Examiner* — Mahidere S Sahle
(74) *Attorney, Agent, or Firm* — Fenwick & West LLP

(57) ABSTRACT

The present invention provides a rapid, high quality iris imaging system. In one embodiment, on-axis illumination is used. A single steering mechanism steers both the camera and the illumination, without parallax issues. The illumination beam can be combined along the camera's optical axis before or after the fine steering and focus correction mechanism. In a pre-correction configuration, the iris illumination spot can be reduced in size to be only slightly larger than the iris. In both the pre and post-correction configuration, the eye safety limits will be most critical at the subject, which allows for maximization of the illumination flux.

20 Claims, 6 Drawing Sheets

U.S. PATENT DOCUMENTS

| | | | |
|---|---|---|---|
| 7,280,676 | B2 | 10/2007 | Miura et al. |
| 7,280,678 | B2 * | 10/2007 | Haven et al. ................. 382/117 |
| 7,408,572 | B2 | 8/2008 | Baxter et al. |
| 7,418,115 | B2 | 8/2008 | Northcott et al. |
| 7,428,320 | B2 | 9/2008 | Northcott et al. |
| 7,458,683 | B2 | 12/2008 | Chernyak |
| 7,766,903 | B2 | 8/2010 | Blumenkranz et al. |
| 2002/0093645 | A1 | 7/2002 | Heacock |
| 2002/0097375 | A1 | 7/2002 | Watson et al. |
| 2002/0161356 | A1 | 10/2002 | Bille et al. |
| 2003/0020872 | A1 | 1/2003 | Liang et al. |
| 2003/0025877 | A1 | 2/2003 | Yancey et al. |
| 2003/0163122 | A1 | 8/2003 | Sumiya |
| 2003/0169334 | A1 | 9/2003 | Braithwaite et al. |
| 2003/0174281 | A1 | 9/2003 | Herekar et al. |
| 2004/0145702 | A1 | 7/2004 | Liang |
| 2004/0165147 | A1 * | 8/2004 | Della Vecchia et al. ...... 351/221 |
| 2004/0169817 | A1 | 9/2004 | Grotehusmann et al. |
| 2005/0007603 | A1 | 1/2005 | Arieli et al. |
| 2005/0185138 | A1 | 8/2005 | Wong et al. |
| 2006/0092376 | A1 | 5/2006 | Baek et al. |
| 2006/0098097 | A1 * | 5/2006 | Wach et al. .............. 348/207.99 |
| 2006/0140454 | A1 | 6/2006 | Northcott et al. |
| 2007/0055222 | A1 | 3/2007 | Hohla et al. |
| 2008/0002863 | A1 | 1/2008 | Northcott et al. |
| 2008/0123053 | A1 * | 5/2008 | Mihashi et al. ................ 351/221 |
| 2009/0046899 | A1 | 2/2009 | Northcott et al. |
| 2009/0099558 | A1 | 4/2009 | Wong et al. |
| 2010/0188483 | A1 | 7/2010 | Berger |

OTHER PUBLICATIONS

*IRIS on the Move™ Flexible Design Platform—Multiple Configurations*, Brochure, 2007, 1 page.

*IRIS on the Move™ Portal System Specifications*, Brochure, 2007, 1 page.

*IRIS & Retina Multi- Modal System*, [online], 1 page, retrieved from the URL:<http://retica.com/site/technology/irisretina.htm>.

*HIIDE Series 4*, [online], 2 pages, retrieved on Apr. 23, 2008, retrieved from the URL:<http://www.securimetrics.com/solutions/hiide_specs.html>.

*Pier 2.3*, [online], 2 pages, retrieved on Apr. 23, 2008, retrieved from the URL:<http://www.securimetrics.com/solutions/pier_specs.html>.

* cited by examiner

ON-AXIS ILLUMINATION FOR IRIS IMAGING

CROSS-REFERENCE TO RELATED APPLICATION(S)

This application claims priority from U.S. Provisional Patent Application Ser. No. 60/886,888, filed Jan. 26, 2007, entitled "On-Axis Illumination for Iris Imaging." This application is related to U.S. patent application Ser. No. 11/765,401, filed Jun. 19, 2007, entitled "Iris Imaging Using Reflection From The Eye," and U.S. patent application Ser. No. 11/297,578, filed on Dec. 7, 2005, entitled "Iris Imaging Using Reflection From The Eye." The subject matter of all of the foregoing is incorporated herein by reference in their entirety.

BACKGROUND OF THE INVENTION

1. Field of the Invention

This invention relates to illumination of the human iris for iris imaging, as may be used for biometric identification.

2. Description of the Related Art

One of the most challenging aspects of iris imaging for biometric purposes is arranging to obtain adequate light level at the iris to obtain high signal to noise ratio (SNR) images. The iris has a low contrast and a low albedo scattering very little light back to the iris camera, requiring high illumination levels to obtain good image SNR. At the same time, eye safety limits constrain the amount of illumination that can be used. With modern CCD or CMOS imagers, the noise of the devices is already low enough that the image SNR is dominated by photon (quantum shot) noise at the intensity levels of interest. There is some room for improvement in quantum efficiency, which is currently in the range of 15 to 35% at 850 nm for the best commodity devices. Expensive scientific grade detectors can show quantum efficiency of 90% which is close to the theoretical limit but even at this level of performance detectivity is only improved by a factor of three to six. This leaves three main methods for increasing image SNR: increasing illumination level, increasing exposure time, and increasing numerical aperture.

With respect to increasing illumination levels, the eye safety limit allows for quite generous levels of illumination of the eye. However, the eye safety requirements apply at every accessible point in space. This puts significant constraints on the design of illumination systems, because in practice they are required to be eye safe even if someone looks directly into the illumination aperture. Conventional iris imaging systems predominantly work at a preferred wavelength of 850 nm. At shorter wavelengths, closer to the conventional visible wavelength band, the eye safety limitations become more stringent. Furthermore, at visible wavelengths, light of sufficient intensity may become too bright to look at, thus triggering the aversion response. At longer wavelengths than 850, the eye safety thresholds increase significantly. However, at longer wavelengths, the transparency of the iris material increases, which leads to significant changes in the image morphology. Thus, use of wavelengths significantly longer than 850 nm may result in images that are incompatible with expositing iris coding algorithms and databases. Incompatibility with expositing algorithms does not necessarily obviate the usefulness of longer wavelengths, but will nevertheless impact marketability of a longer wavelength solution. The responsivity of inexpensive silicon based detectors also falls very rapidly as wavelengths increase past 850 nm, making detection of long wavelength light increasingly expensive.

With respect to increasing exposure time, the fact that the subject may be moving constrains the illumination time in conventional non-tracking systems. Increasing the illumination time increases the possibility of motion blur.

With respect to increasing the numerical aperture, it is well known that for a given image scale, larger lenses capture more light. There are cost constraints to building very fast lenses, but more significant is the effect on depth of field. Because the subject may be moving, the depth of field of the imaging device has to match the maximum expected depth movement of the subject over the exposure time. If the camera is statically focused, a smaller depth of field also limits the probability that the subject will be within the focus range. Increasing the numerical aperture without increasing the detector pixel pitch, can lead to aliasing errors, where high frequency image structure appears incorrectly as low frequency features. Both effects can be somewhat ameliorated by deliberately reducing the fidelity of the lens.

SUMMARY OF THE INVENTION

The present invention provides a rapid, high quality iris imaging system. Light illuminates the subjects' eyes. Reflection from the eyes (e.g., retro-reflection from the retina or glint reflection from the cornea) is used to steer (and preferably also focus) a high resolution camera to the eyes in order to capture images of the irises. The camera captures images of irises with sufficient resolution for biometric identification. Real-time steering and focus correction may extend the usable exposure time, thus allowing good images under lower illumination levels than otherwise possible.

In one embodiment, on-axis illumination is used to illuminate the subjects' eyes. A single steering mechanism steers both the camera and the illumination, without parallax issues. In one implementation, the illumination beam is combined with the imaging beam along the camera's optical axis on the subject side of the iris camera objective lens. In another implementation, the illumination beam is combined with the imaging beam along the camera's optical axis before the fine steering and focus (and possibly higher order aberrations) correction mechanism. In a pre-correction configuration, the iris illumination spot can be reduced in size to be only slightly larger than the iris. In both the pre and post-correction configuration, the eye safety limits will be most critical at the subject, which allows for maximization of the illumination flux.

Other aspects of the invention include methods corresponding to the devices and systems described above.

BRIEF DESCRIPTION OF THE DRAWINGS

The invention has other advantages and features which will be more readily apparent from the following detailed description of the invention and the appended claims, when taken in conjunction with the accompanying drawings, in which:

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE PREFERRED EMBODIMENTS

1. Portal Illumination

Figure 1:
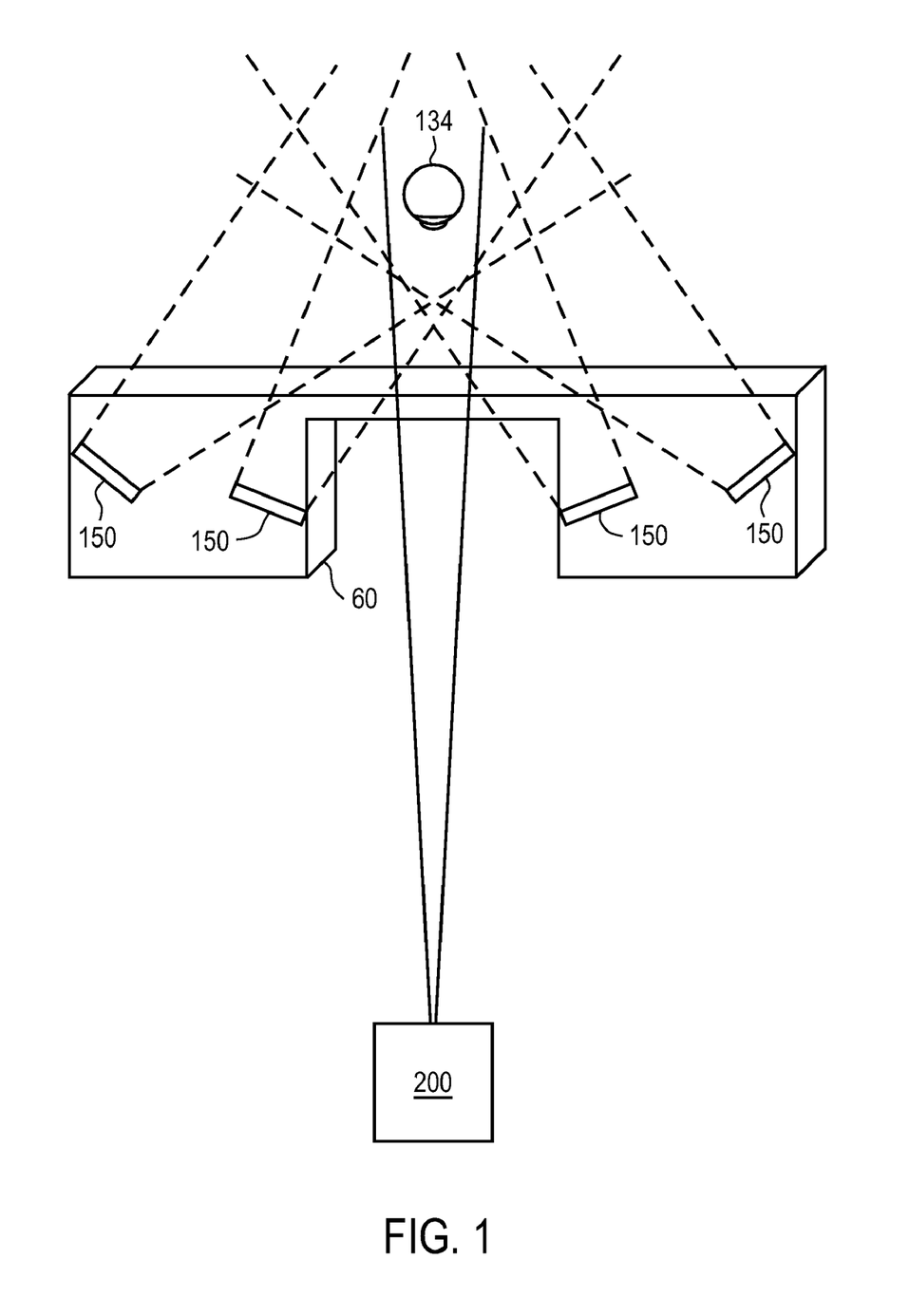
FIG. 1 is an illustration of an iris imaging system using off-axis illumination mounted on a portal.

FIG. 1 is an illustration of an iris imaging system using off-axis illumination devices 150 mounted on a portal 60. The iris imaging system includes an imaging subsystem 200. The system is designed to capture iris images of many eyes 134, typically without the active cooperation of the subjects. In one application, the subjects are passing through a portal 60 (such as a doorway, hallway, or metal detector); the iris imaging system captures iris images as the subjects pass through. Examples include corridors, turnstiles, toll booths, elevator doors, escalators and parking garage entrances. Other examples include checkout lines or other queues, crosswalks, sidewalks and roadways.

This situation typically is "uncooperative," meaning that the subjects are not actively cooperating in the iris imaging. For example, they are not placing their heads into a device to allow capture of iris images. Rather, they are simply walking through the portal 60 and the imaging subsystem 200 captures their iris images as they do so. They may even be unaware that the system is imaging their irises. If stealth is important, the wavelengths should be chosen to be non-visible. Eye safety scales quite rapidly around the 850 nm wavelength. Thus, when using a broad band source it may therefore be advantageous from an eye safety perspective to use band pass or low pass filters to eliminate shorter wavelengths.

The portal 60 may be constructed to hold numerous illumination devices 150. In the example shown in FIG. 1, four illumination devices 150 are present, but more or less may be present. Having a portal 60 that holds illumination devices 150 mitigates eye safety concerns by placing the illumination sources closer to the subject, which means there is much less difference between illumination levels at the illumination devices 150 and the subject's eyes 134. This approach also allows for the use of several independent banks of illuminators, which converge around the preferred subject position. The illuminators may be of the same or different kinds, wavelengths, and intensities, depending on the desired application. Under most situations, well separated sources can be treated independently for eye safety considerations, which allows the illumination level to scale linearly with the number of sources.

Although the iris imaging system using off-axis illumination devices 150 mounted on a portal 60 is useful in some situations, the portal 60 constrains the situations where such a system can be used. Secondly, the use of multiple illumination devices 150 can also cause multiple glint images on the eye. It is probable that at least some of these glints will obscure parts of the iris image, thereby reducing the accuracy of the biometric identification.

2. On-Camera Illumination

The term "on-camera illumination" is used herein to encompass several system designs wherein the illumination source is placed very near the imaging camera. In contrast to the portal solution described above, this typically results in a very narrow angle between the illumination direction and the camera direction, referred to herein as "near on-axis illumination," or the illumination beam is directed along the camera's optical axis, referred to herein as "on-axis illumination."

Traditionally, it has been thought that a large angle is necessary to improve the contrast of images. This was assumed to be due to the three-dimensional structure of the iris. However, experiments conducted by the inventors have shown that the iris image contrast is not significantly reduced by using on-axis or near on-axis illumination.

An advantage of on-camera illumination is that the camera and illuminator can be housed in a single package, which makes deployment of the system much easier and its use more convenient. A further benefit of on-camera illumination is that the glint from the iris illuminator source will be positioned within the eye pupil, and will not contaminate the area of the iris image available for coding.

As has been described in U.S. patent application Ser. No. 11/765,401, filed Jun. 19, 2007, entitled "Iris Imaging Using Reflection From The Eye," which has been incorporated herein by reference, the term "wavefront sensing" includes determination of not only tip-tilt or location, but also includes focus, and potentially sensing of higher order aberrations. As has also been described therein, both the corneal glint return and the retinal retro-reflection (redeye return) can be used for wavefront sensing using a wavefront sensor ("WFS"). In one embodiment, if a retro-reflection signal is used, the retro-reflection return is enhanced by positioning the illumination source as close to on-axis as possible. In another embodiment, if a glint return is used, then moving the illumination source off-axis reduces confusion caused by the retro-reflection return by reducing its level.

Figure 6:
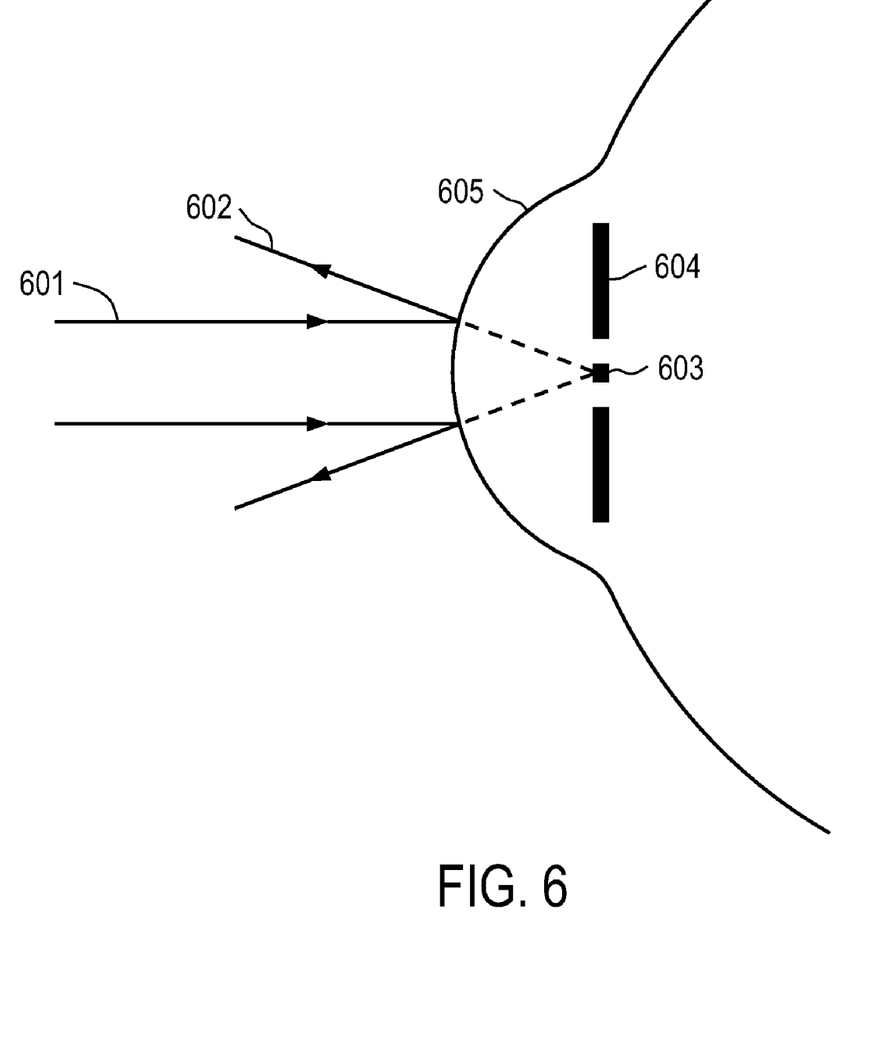
FIG. 6 is an illustration of the differing thickness of the cornea in front of the iris and the position of a glint as seen by a camera, in accordance with an embodiment of the invention.

FIG. 6 is an illustration of the differing thickness of the cornea in front of the iris and the position of a glint as seen by a camera, in accordance with an embodiment of the invention. The incoming illumination 601 reflects from the surface of the cornea 605. In the case of glint reflection, the specular reflection 602 from the cornea surface 605 produces a virtual image 603 of the illumination source. The virtual image 603 is the position of the glint as seen by the camera. This virtual image 603 is significantly de-magnified, and appears very close to the eye pupil plane and the location of the iris 604 in the eyeball, and is therefore close to optimal for determining the correct focus for imaging the iris structure in some embodiments.

Due to the varying thickness of the cornea across the iris, some defocus towards the edges of the cornea is present in some embodiments. The focus of the iris is a function of radius; defocus degrades the image quality towards the iris outer edge. In most situations, the degradation will not significantly affect the biometric signal.

In one embodiment, the focus set-point of the system can be deliberately moved over time such that a series of images can be taken at slightly different focus. These images can then be combined to obtain an optimally sharp image over the whole iris diameter. Correction of a corneal defocus effect is also possible by design of the optical imaging system with a compensating field-dependent focus aberration. Compensation of focus through successive images can be performed by changing the control software to deliberately add focus offsets to the computed best focus, as derived by the wavefront sensor based on the glint or retinal return. A focus determination could also be made by analyzing the contrast of the iris image at the relevant offset, but this would slow down focus tracking substantially. In one embodiment, combination of the images can best be performed by using a weighted average of the images, where the weighting function is dependent on the spatial frequency content of the image.

A serious concern for some applications of iris biometric imaging is the possibility of spoofing the system by using a fake iris image. A fake image may be an image of an eye, a fake eyeball, or a contact lens worn over the real iris. Methods for reliably detecting a range of spoofing techniques would be crucial to the acceptance of iris biometrics in some of these applications. A patterned contact lens fabricated to spoof iris scanning will place the iris pattern on the surface of the cornea. This means that the contact lens pattern will be out of focus relative to a true iris, and will display a significantly different pattern of sharpness versus focus distance from the glint defined focus plane. For a patterned contact lens that lies on the surface of the cornea, the maximum defocus with respect to the glint defined focus plane will be near the center of the contact lens, with focus improving at larger radii. Thus, a method of detecting a patterned contact lens spoof is as follows. An expected focus plane is determined from a glint reflection from the eye. As compared to the expected focus plane, an amount of defocus near the center of the iris image, i.e., the inner border of the iris, is determined. Also as compared to the expected focus plane, an amount of defocus near the outer edges of the iris image, i.e., the outer border of the iris, is determined. If the amount of defocus near the inner border of the iris image is greater than the amount of defocus near the outer border of the iris image, then the image is determined to be not of an authentic iris. In some systems, a signal is output indicative of this conclusion. Alternatively or additionally, access is denied to a resource protected by the biometric identification system. Accordingly, a contact lens spoof and other related spoofing techniques can be identified and defeated.

Anti-spoofing can also be provided using several other methods. For instance, the eye pupil radius naturally oscillates in a motion known as hippos, which aids the eye in adjusting to varying light conditions. This motion can be sensed by looking at a series of images, provided that the images are all of good quality. The eye pupil radius will also adjust in response to changes in ambient illumination, which can also be used for spoofing detection if some control of the ambient light level is available. When the pupil size changes, the iris image stretches as if it were an elastic sheet. Failure to observe iris stretching would be a strong indication that the pattern comes from a fixed image, such as a contact lens.

In another embodiment, the glint image can also be used to determine the point spread function (PSF) for each iris image. This PSF can then be used for deconvolution or other post processing. However, in many cases the glint image may be over-exposed, thus obviating its usefulness. This potential for overexposure of the glint image can be addressed in several ways. First, a ghost reflection from a surface of an optical element within the iris imaging system can be deliberately introduced which produces a low intensity copy of the glint image. Alternatively, a custom low intensity glint source spatially offset from the main glint source can be provided for the purpose of recording the PSF. As another alternative, signals from the WFS may be recorded over the duration of the iris image exposure, to enable reconstruction of the system PSF in software. The WFS recordings may be used with either glint images, or pupil retro-reflection images, though processing is somewhat simpler in the case of glint images. In either case, differences between the optical path to the iris imager and the WFS may need to be calibrated, in order that measurements in the WFS can be used to accurately predict the PSF in the iris imager camera. Any deconvolution or post processing may need to account for the variability of the PSF over the field, particularly if no compensation for the variable corneal focus discussed in above is applied. The variability can be calibrated from calculated and computed field dependent corrections applied to the main PSF according to techniques known to those of skill in the art. In any of these cases, the on-axis or near on-axis illumination makes recording the PSF more practical, since the glint image is placed over the pupil, where there is no background image structure to contaminate the measurement of the PSF.

A. Near on-Axis Illumination

Figure 2:
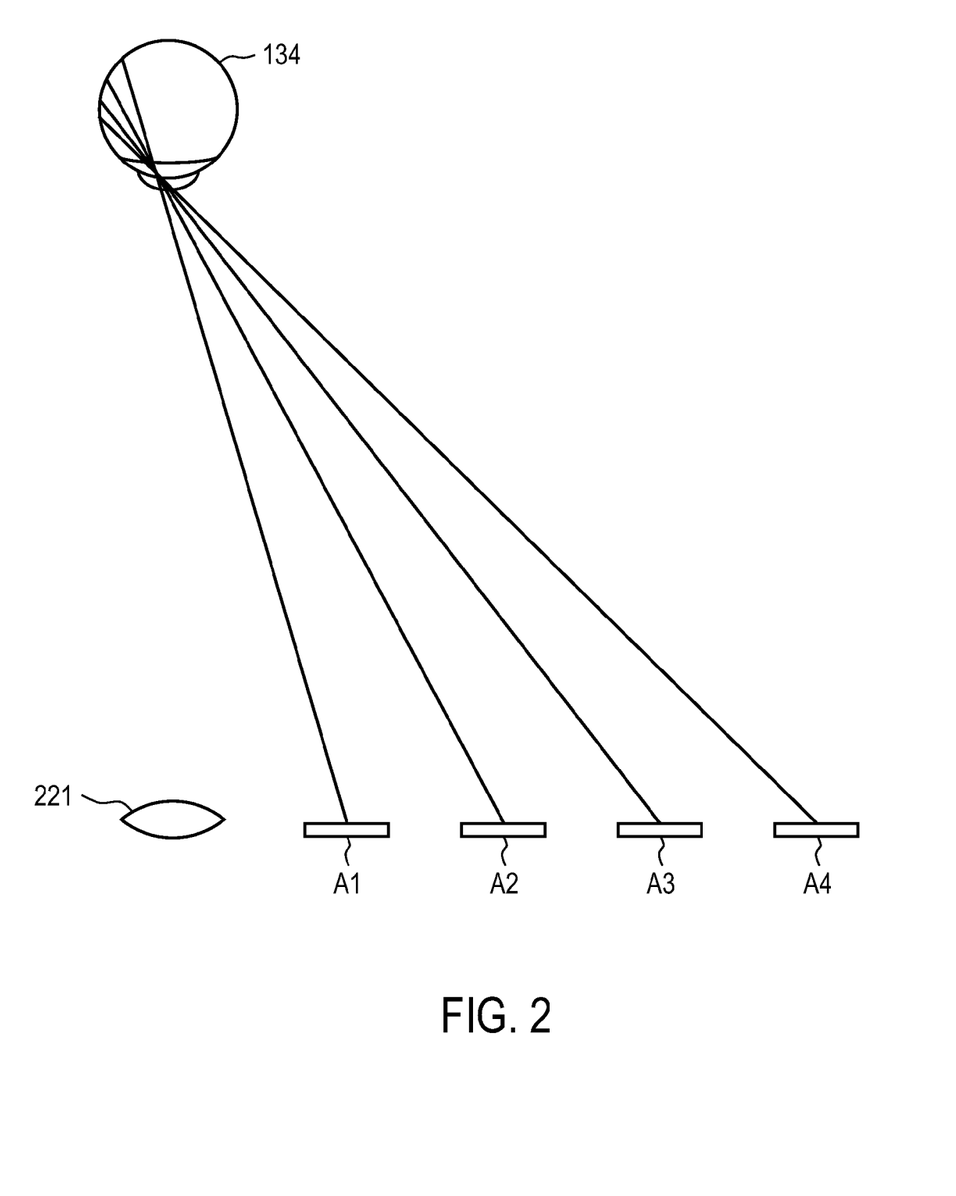
FIG. 2 is an illustration of an array of near on-axis illumination sources.
Figure 3:
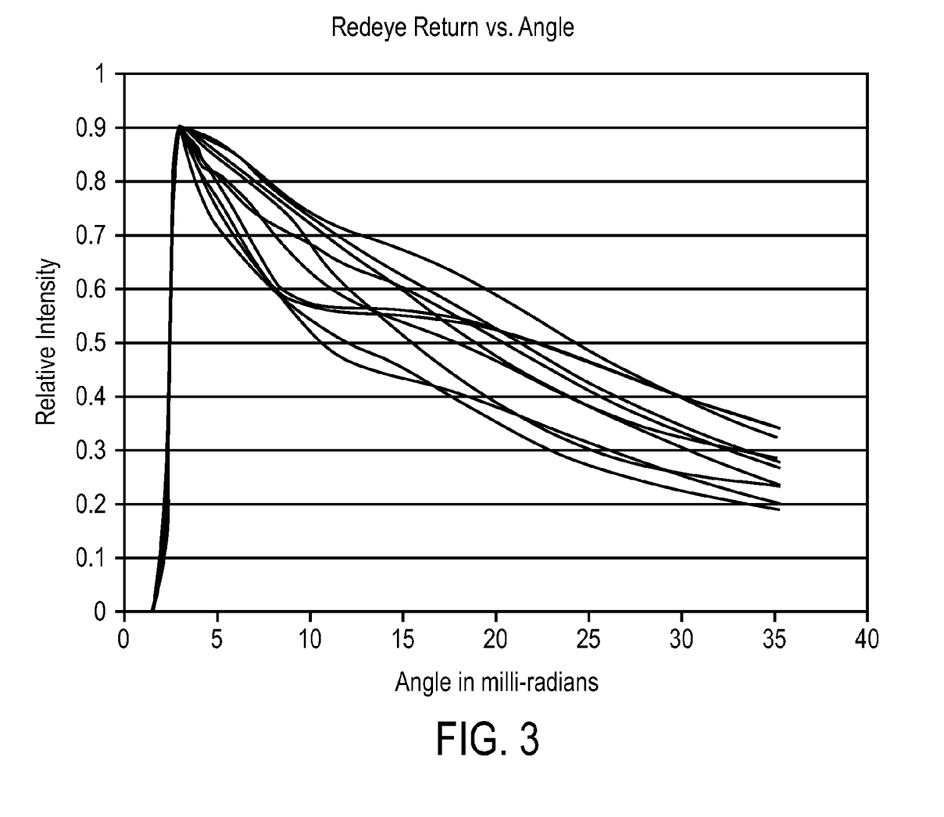
FIG. 3 is a graph illustrating the relationship between the intensity of redeye return and the angle of illumination.

FIG. 2 illustrates a non-steerable array of near on-axis illumination sources. Light sources A1-A4 are any sources of sufficient brightness to illuminate the iris at the level required to capture an iris image. Light sources A1-A4 are positioned at various off-axis distances from the objective lens 221 of the iris camera; larger distances give lower redeye return. FIG. 3 illustrates this relationship between the angle in milli-radians (between the camera axis and the illumination source) and the redeye return for several sample cases. On average, the level of red-eye drops by about a factor of two for every degree off-axis of the illuminator. The inventors have observed that the level of red-eye at an angle is smaller under bright conditions when the pupil is at its smallest extent. The inventors have also observed a lower red-eye for corrected eyes. One inference from this is that the level of red-eye is dependent on the quality of the subject's vision, so will be quite variable among the population. As an example, young children, who tend to have fairly poor vision, tend to show a much larger off-axis red-eye return than adults.

In one embodiment, the iris illumination sources illuminate the whole volume of space in which iris images may be captured, referred to herein as the "capture volume." Illumination of the entire capture volume, referred to herein as "flood illumination" is typically limited to shorter ranges in situations where the subject position can be relatively well constrained. In a typical installation, the illumination will diverge quite strongly from the illumination source to cover the capture volume. The illumination divergence means that eye safety constraints are highest very close to the illumination source, which limits the illumination at the subject to levels that are significantly below the eye safety limits.

The illumination sources shown in FIG. 2 can be made steerable by placing them on a gimbal or by using a steering mirror to direct the light. If a steering mirror is used, the same steering mirror may be used to both direct the imaging path, and the illuminator beam. Alternatively, the imaging subsystem and the illumination sources can be packaged jointly, and the whole instrument can be placed on a gimbaled mount. When a steering mechanism is used, the illuminated area can be significantly smaller than in the flood illumination case described above. This requires a more collimated beam from the illumination source. When a nearly collimated beam is used, the eye safety limit is not strongly dependent on distance, which allows for significantly stronger subject illumination without exceeding safety limits close to the illumination source. Such a near-collimated steered illumination source also allows for high illumination levels to be delivered at substantial standoff distances. Using this mechanism it is possible to envisage eye safe iris imaging at distances of several tens of meters. For example, the inventors have demonstrated the common steering mirror implementation discussed herein at a distance of 18 meters in the laboratory.

An adaptive optics system (not shown in FIGS. 1-2) may be used to achieve fast, fine tracking of the subject and optionally also focus adjustment for the image capture. Fast active control of the focus can allow for higher numerical aperture by actively correcting the focus to ensure that the subject is always within the camera depth of field. The adaptive optics system may be driven by eye reflection from the subject's eye 134. If the off-axis illumination source glint image is being used to drive wavefront correction (including tracking and focus), then a face tracker using ambient illumination or a non-steered flood illumination can be used to locate targets so that the illumination source can be positioned on the subject's eye before wavefront correction begins.

B. Parallax Error Compensation

Larger off-axis angles give lower redeye returns but also increase the parallax between the direction of the iris camera and the illumination source. Parallax can be accommodated in several ways.

One way to accommodate parallax is to increase the divergence of the steered beam so that it is wide enough to encompass any parallax error and still fully illuminate the subject's eye. This will require a brighter source and some reduction in on-axis illumination intensity to accommodate eye safety limits. A wide beam that can accommodate parallax will not generally require precision guiding, so a simple inexpensive steering mechanism will suffice. This approach is also appropriate if the whole camera system is on a gimbal.

Another way to accommodate parallax is by guiding the light source independently using face tracking or deliberately enhanced redeye reflection (retinal retro-reflection). In this case, the guiding camera would be placed near the illumination array and co-steered with this array. This arrangement would increase the complexity of initial acquisition on the iris camera system, requiring either a second tracking camera or explicit calculation of the parallax angle.

Another way to accommodate parallax is by explicit calculation of the subject range and open loop control of the differential offset. The subject range may be determined using a range calculation module. The range calculation module may determine range using any of several focus acquisition methods. The range calculation module may determine subject distance using stereoscopic imaging. The range calculation module may also determine distance using a laser or ultrasonic range finder. The simple expedient of placing a mat on the floor containing pressure sensitive switches could also be used. The range calculation module may receive input from an off-axis camera that notes the subject position relative to a fixed background pattern to determine range. These or any other range detection devices could be used to determine the approximate subject range for the purpose of parallax correction. Alternatively, for a small field of view illumination source, a close loop control of the illumination source using images from a face camera, or similar wide field camera can be used. This control obviates the need for independent distance measurement, since the displacement of the image relative to the expected position would give a measure of subject distance.

C. On-Axis Illumination

Figure 4:
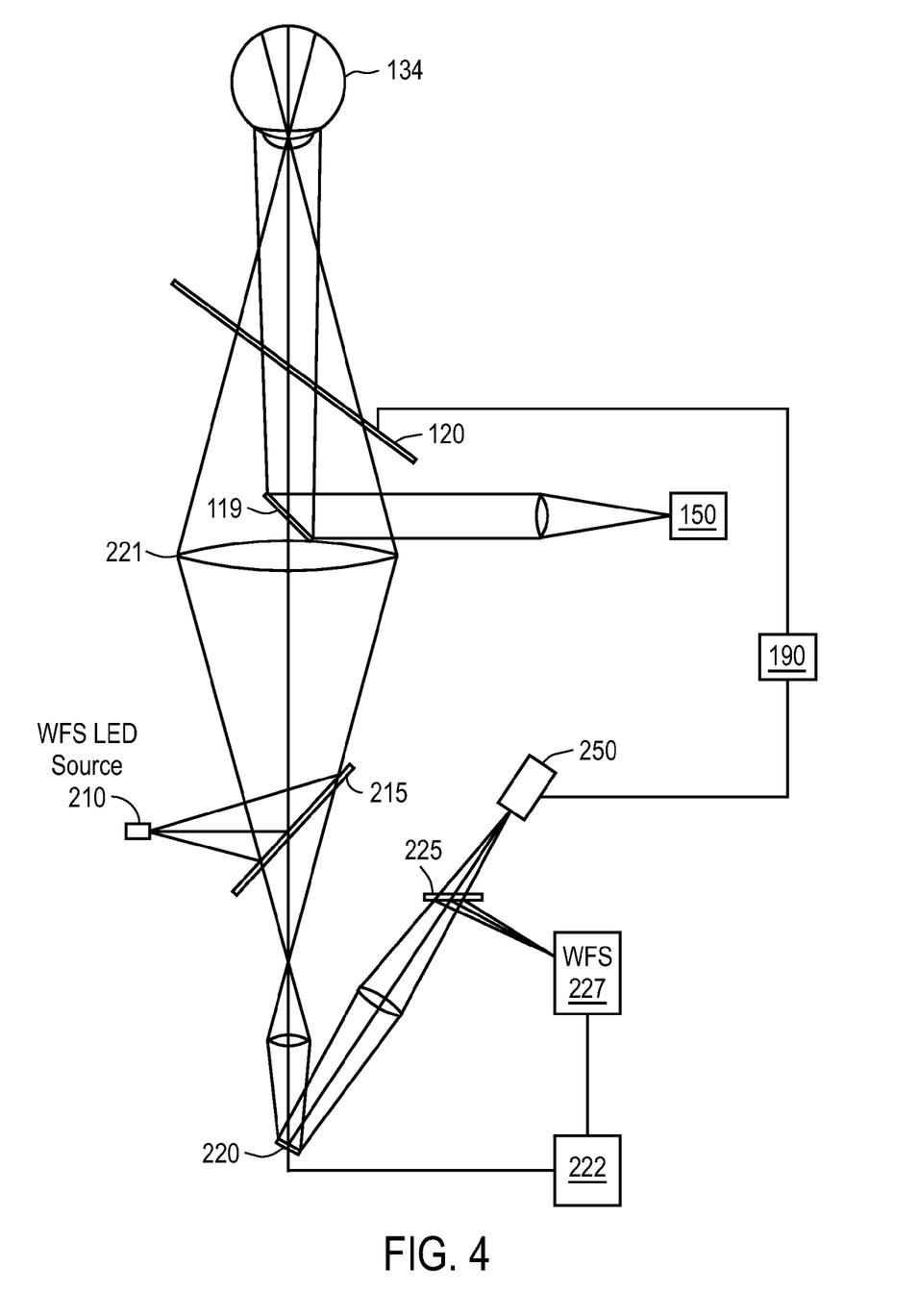
FIG. 4 is an illustration of an iris imaging system using on-axis illumination in accordance with an embodiment of the invention.

FIG. 4 illustrates an iris imaging system using on-axis illumination according to an embodiment of the present invention. In this example, the illumination for iris imaging is provided by illumination device 150. Light from illumination device 150 is combined into the on-axis optical path to the subject's eye 134 using a beam splitter or other optical element 119. The imaging subsystem 200 includes a light source 210, a beam splitter 215, a deformable mirror 220, a beam splitter 225, a wavefront sensor 227, a camera 250, and a controller 222. The iris imaging system also includes a coarse tip-tilt steering mirror 120 controlled by controller 190, which is used both to direct the illumination from illumination device 150 and to steer the imaging subsystem 200. In FIG. 4, the steering mirror 120 is depicted as a line through the optical beam but, for simplicity, reflection off the steering mirror is not shown (i.e., the optical path is unfolded with respect to steering mirror 120). Various lenses (or other optics) are used to collimate, focus, image or otherwise relay the optical beams throughout the system.

Light produced by illumination device 150 reflects off beam splitter 119, is directed by steering mirror 120 to illuminate the subject's eye 134. Light from the illuminated eye 134 reflects back to the steering mirror 120, passes through beam splitter 215, reflects from deformable mirror 220, and passes through beam splitter 225 to camera 250 which captures the iris image. One advantage of steering imaging subsystem 200 together with the light from the illumination device 150 is that a fixed relationship between the wavefront sensor 227, the camera 250, and the illumination device 150 is maintained. This arrangement also reduces the requirements for the imaging camera field of view, considerably simplifying its optical design.

In one embodiment, the imaging subsystem 200 operates as follows. Wavefront sensor light source 210 illuminates the eye 134. Light produced by light source 210 reflects off beam splitter 215, propagates through lens system 221 and is directed by steering mirror 120 to the eye 134. A portion of the light enters the eye 134, which retro-reflects light back along the same path 120-221. The return light passes through the beam splitter 215, reflects off deformable mirror 220 and is directed by beam splitter 225 to the wavefront sensor 227. The wavefront sensor 227, controller 222 and deformable mirror 220 form an adaptive optics loop that is driven based on the retro-reflected light from the eye 134. The adaptive optics loop is used to steer (and preferably also focus) the camera 250 to the eye 134 in order to capture images of the irises.

In the example of FIG. 4, the reflection from the eye is a retinal retro-reflection. Alternatively, the front surface of the eye acts as a partial mirror with about 4% reflectivity. Reflections from this surface form a glint that can be used to steer the imaging subsystem 200 instead of the retro-reflection. For example, the system of FIG. 4 can be modified so that the light source 210 illuminates eye 134, but the wavefront sensor 227 is driven by a glint reflection from the eye rather than a retro-reflection. A resulting advantage is that the size and shape of the glint is not a strong function of the distance to the subject.

In yet another embodiment, a glint reflection of the cornea surface of the eye 134 or a retro-reflection from of eye 134 from illumination device 150 is used to drive the adaptive optics loop, thus eliminating the WFS light source 210 and the beam splitter 215 from the optical arrangement.

While adaptive optics can be used in many applications to correct for high order aberrations, in this case, the adaptive optics loop is used mainly for fast tracking of the eye 134 (i.e., correction of tip/tilt errors in the wavefront) and preferably also for focus correction. This keeps the iris 134 within the field of view of camera 250 and also focuses the camera (if focus correction is implemented).

Traditional adaptive optics systems, such as those developed for astronomy, may be too large, complex and/or costly to be effectively used in applications such as iris imaging. However, recent advances by AOptix Technologies of Campbell, Calif., have resulted in the development of complete adaptive optics systems, including electronics, that achieve sizes smaller than a shoe box. The AOptix adaptive optics systems require less than 25 W of power and can reliably operate unattended for extended periods of time. The small size, weight and power and high reliability of the AOptix adaptive optics systems make them suitable for applications such as the iris imaging applications described herein.

In these more compact systems, the deformable mirror 220 is a deformable curvature mirror based on applying different voltages across different areas of a piezoelectric material, thus causing deformation. Further details for this type of deformable mirror are described and shown in U.S. Pat. No. 6,464,364, "Deformable Curvature Mirror," filed Jan. 25, 2001 and issued Oct. 15, 2002, by J. Elon Graves and Malcolm J. Northcott; U.S. Pat. No. 6,568,647, "Mounting Apparatus for Deformable Mirror," filed Jan. 25, 2001 and issued May 27, 2003, by J. Elon Graves and Malcolm J. Northcott; and U.S. Pat. No. 6,721,510, "Atmospheric Optical Data Transmission System," filed Jun. 16, 2001 by J. Elon Graves and Malcolm J. Northcott. Furthermore, the wavefront sensor 227 is a wavefront curvature sensor based on defocused pupil images. Further details for this type of wavefront curvature sensor are described and shown in U.S. Pat. No. 6,452,145, "Method and Apparatus for Wavefront Sensing," filed May 26, 2000 and issued Sep. 17, 2002, by J. Elon Graves and Malcolm J. Northcott; and U.S. Pat. No. 6,721,510, "Atmospheric Optical Data Transmission System," filed Jun. 16, 2001 by J. Elon Graves and Malcolm J. Northcott. All of the foregoing are incorporated herein by this reference. Other types of commonly known deformable mirrors and wavefront sensors may also be suitable for iris imaging.

Figure 5:
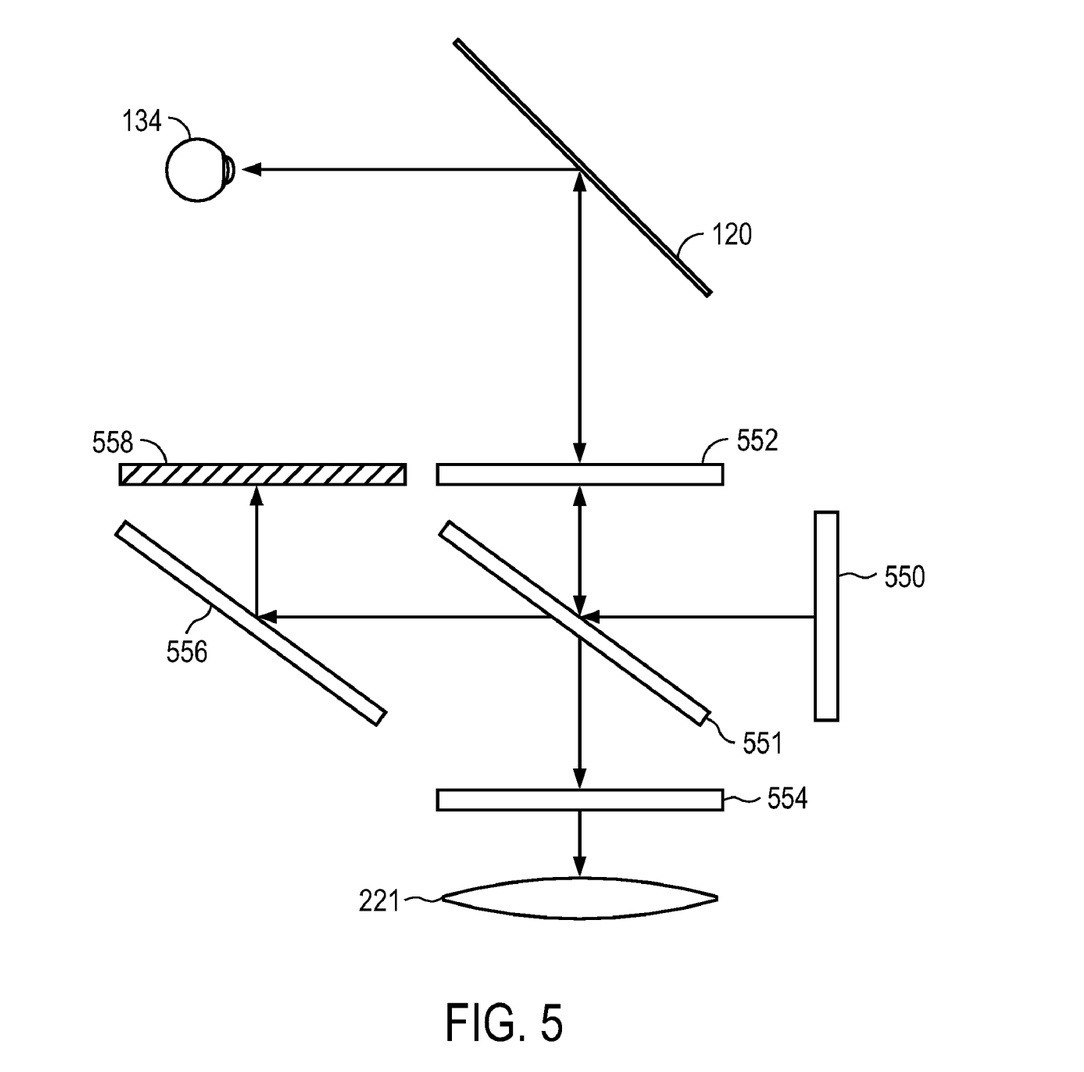
FIG. 5 is an illustration of another iris imaging system using on-axis illumination in accordance with another embodiment of the invention.

FIG. 5 shows one example of an optical arrangement for an iris imaging system having an on-axis illumination source. As discussed above, on-axis illumination maximizes the retinal retro-reflection. Thus, high quality optics should be used to prevent degradation of the iris image by scattered light.

In one embodiment, the optics prevents local back reflection into the iris camera optics by using polarization. Light from illumination source 550 is directed toward polarizing beam splitter 551 which splits the light into two beams having opposite polarizations. One of the beams is directed along a common optical axis with the camera through quarter wave plate 552, and reflects off steering mirror 120 toward the subject's eye 134. The other beam is directed to an anti-reflection coated absorbing neutral density filter 556. Any remaining reflections from the filter 556 are absorbed by a black beam stop 558. The light returning from the subject's eye 134 reflects from steering mirror 120, passes through the quarter wave plate 552, the polarizing beam splitter 551, and the polarizing filter 554 to reach the camera's objective lens 221. Thus, stray reflections from the beam combining optics (which preserve polarization) are prevented from entering the camera's objective lens 221 by this arrangement. Since the scattered light from the iris image does not preserve polarization, it passes through to the camera's objective lens 221. In an alternative embodiment, neutral beam splitters can also work to reduce the local back reflections into the iris camera optics.

In the configuration shown, the illumination beam is steered by the same mechanism, the steering mirror 120, that accomplishes coarse steering for the iris camera. One advantage of on-axis illumination is that a single steering mechanism can steer both the camera and the illumination, without parallax issues. In the mechanism as shown, the illumination beam is combined with the imaging beam on the subject side of the iris camera objective lens 221. It is also possible to combine the illumination beam with the camera beam before the fine steering and focus (and possibly higher order aberrations) correction mechanism. In a pre-correction configuration, the iris illumination spot can be reduced in size to be only slightly larger than the iris. In both the pre and post-correction configuration, the eye safety limits will be most critical at the subject where the beam will be smallest, which allows for maximization of the illumination flux.

D. Bright Field Pupil Segmentation

An initial step in iris recognition processing is to determine which areas of the image comprise the actual iris. This is a common image processing step that is usually referred to as "segmentation." For the purpose of iris recognition, segmentation comprises at least the following steps:
(a) Finding the inner border between the iris inner edge and the eye pupil.
(b) Finding the outer iris border, between the iris and the sclera.
(c) Finding the upper and lower eye lid boundaries.
(d) Identifying any eye lashes which overlap the iris image.
(e) Identification of any glints that overlay the iris image. Glints may be due to reflection from the illumination source or other lights.

On a statistical basis, iris structure tends to be concentrated towards the inner edge of the pupil, making segmentation of the inner iris border, step (a), especially critical for consistent and accurate iris identification.

In an off-axis illumination configuration, pupil segmentation finds the border between the iris and the dark pupil in step (a). Since the iris contains structure that extends right up to the pupil border, dark areas in the iris can perturb the pupil finding algorithm. The net result of dark areas will be that the compute pupil border will erroneously extend into the iris area. The extent of such errors will depend on the SNR of the image, and may therefore be somewhat variable between images. The boundary error may also depend on the size state of accommodation (pupil size) at the time that the image is taken.

In an on-axis illumination configuration, the pupil becomes a bright area due to the retinal retro-reflection of the on-axis illumination. The edge of the pupil is sharply defined, since the iris structure efficiently blocks scattered light from the retina returning to the camera. Furthermore, the pupil is defined by a bright area which will typically have significantly higher SNR than the surrounding iris area. Both of these effects make finding the inner iris border more accurate and more consistent.

3. Accommodation Response

At visible wavelengths the eye accommodation response ensures that the iris will close down when exposed to a bright light. There are several advantages in iris imaging to triggering the accommodation response, including reduced red-eye return and improved iris images. The total red-eye return is proportional to approximately the area of the eye's pupil. The divergence of the red-eye return decreases quite strongly with pupil size. Thus, for an off-axis illuminator, decreasing the size of the eye pupil can reduce red-eye very strongly. This red-eye reduction phenomenon is used in standard photography, where a short pre-flash is used to reduce red-eye in images. Secondly, when the pupil closes down in the accommodation response, the iris is stretched to cover the increased area. In the initial image, it is advantageous to have the iris stretched to its maximum area. Increasing the area of the iris increases the total number of image pixels that contain iris information, and increases the total amount of signal in the iris image. Biometric iris image analysis software transforms the resulting images to compensate for the effects of iris stretching.

A. Mixed Visible and IR Illumination

At non-visible (including 850 nm) wavelengths, the ultimate barrier to increasing illumination light levels is the eye safety considerations. At visible wavelengths, the aversion response is likely to place practical limits on brightness more than formal eye safety limits. At visible wavelengths the eye accommodation response ensures that the iris will close down when exposed to a bright light, which leads to an assumed eye pupil diameter of 3 mm. The eye safety limits for IR wavelength are usually computed using a 7 mm pupil, since it is assumed that the accommodation response will not necessarily cause the pupil to accommodate to its minimum size. However, if the environment is always bright enough to trigger the maximum accommodation response, it is permissible to use the 3 mm pupil diameter in calculations, thus increasing the permissible light levels. In some applications it may therefore be advantageous to apply visible stimulus as well as IR illumination, the main purpose of the visible wavelength stimulation being to trigger accommodation. In situations where a face camera is included with the iris imaging system, this visible light may also provide light for the face imaging camera.

B. Liveness Testing

The diameter of the pupil in a live eyeball is constantly changing as the eye seeks optimal accommodation. By analyzing a series of images and looking for changes in pupil diameter, many possible spoof attacks on iris imaging for biometric identification can be defeated. For instance, images on eyes or artificially constructed eyes will not display a variable pupil diameter. Also, patterned contract lenses will probably exhibit a fixed pupil diameter or will exhibit anomalous conformal stretching of the iris. Therefore, in situations where spoofing is thought to be a serious threat, the brightness of any visible illumination component can be modulated in order to trigger an enhanced accommodation response.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

What is claimed is:

1. An iris imaging system comprising:
    a steerable collimated illumination source to illuminate a subject's eye;
    a camera for capturing an image of the illuminated iris of the subject's eye with sufficient resolution for biometric identification, wherein the illumination source is near on-axis with respect to an optical axis of the camera; and
    an adaptive optics loop to steer and focus the camera to the subject's eye, the adaptive optics loop comprising a deformable mirror, a wavefront sensor and a controller coupled between the deformable mirror and the wavefront sensor, the controller configured to adjust the deformable mirror based on a wavefront sensed by the wavefront sensor, the deformable mirror steering and focusing the camera to the subject's eye.

2. The iris imaging system of claim 1, wherein the adaptive optics loop steers and focuses the camera to the subject's eye based on a retinal retro-reflection.

3. The iris imaging system of claim 1, wherein the illumination source and the camera are housed in a single package.

4. The iris imaging system of claim 1, wherein the collimated illumination source triggers a maximum accommodation response.

5. The iris imaging system of claim 4, further comprising an infrared light source for illuminating eyes of the subjects for iris imaging.

6. The iris imaging system of claim 1, wherein an intensity of the illumination source is varied to trigger a varying accommodation response for liveness testing.

7. The iris imaging system of claim 1, further comprising a range calculation module for determining a distance to the subject.

8. An iris imaging system comprising:
    a nearly collimated illumination source to illuminate a subject's eye;
    a camera for capturing an image of the illuminated iris of the subject's eye with sufficient resolution for biometric identification;
    an optical element for combining light from the illumination source into an on-axis optical path from the camera to the subject's eye;
    a steering mirror for steering light from the illumination source to the subject's eye and from the subject's eye to the camera;
    an adaptive optics loop to focus the camera to the subject's eye, the adaptive optics loop comprising a deformable mirror, a wavefront sensor and a controller coupled between the deformable mirror and the wavefront sensor, the controller for adjusting the deformable mirror based on a wavefront sensed by the wavefront sensor, the deformable mirror focusing the camera to the subject's eye.

9. The iris imaging system of claim 8, wherein the optical element comprises a polarizing beam splitter.

10. The iris imaging system of claim 9, further comprising a polarizing filter positioned between the polarizing beam splitter and an objective lens of the camera to prevent reflections from the polarizing beam splitter from entering the camera.

11. The iris imaging system of claim 8, wherein the nearly collimated illumination source triggers a maximum accommodation response.

12. The iris imaging system of claim 11, further comprising an infrared light source for illuminating eyes of the subjects for iris imaging.

13. The iris imaging system of claim 8, wherein an intensity of the illumination source is varied to trigger a varying accommodation response for liveness testing.

14. The iris imaging system of claim 1 wherein the adaptive optics loop steers and focuses the camera to the subject's eye based on a glint reflection.

15. The iris imaging system of claim 1 wherein the adaptive optics loop additionally comprises a wavefront sensor light source to drive the wavefront sensor.

16. The iris imaging system of claim 1 wherein the illumination source is further configured to drive the wavefront sensor.

17. The iris imaging system of claim 8, wherein the adaptive optics loop focuses the camera to the subject's eye based on a retinal retro-reflection.

18. The iris imaging system of claim 8 wherein the adaptive optics loop focuses the camera to the subject's eye based on a glint reflection.

19. The iris imaging system of claim 8 wherein the adaptive optics loop additionally comprises a wavefront sensor light source to drive the wavefront sensor.

20. The iris imaging system of claim 8 wherein the illumination source is further configured to drive the wavefront sensor.

* * * * *